(12) United States Patent
Mandal et al.

(10) Patent No.: US 9,645,269 B2
(45) Date of Patent: *May 9, 2017

(54) ULTRASONIC IMAGING IN WELLS OR TUBULARS

(71) Applicant: Halliburton Energy Services, Inc., Houston, TX (US)

(72) Inventors: Batakrishna Mandal, Missouri City, TX (US); Clovis Bonavides, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 745 days.

This patent is subject to a terminal disclaimer.

(21) Appl. No.: 14/036,545

(22) Filed: Sep. 25, 2013

(65) Prior Publication Data

US 2014/0071790 A1    Mar. 13, 2014

Related U.S. Application Data

(60) Continuation of application No. 12/621,746, filed on Nov. 19, 2009, now Pat. No. 8,576,660, which is a
(Continued)

(51) Int. Cl.
*G01V 1/40* (2006.01)
*G01V 1/30* (2006.01)
(Continued)

(52) U.S. Cl.
CPC ............ *G01V 1/306* (2013.01); *G01N 29/11* (2013.01); *G01N 29/348* (2013.01);
(Continued)

(58) Field of Classification Search
CPC ........ G01V 1/50; G01V 1/44; E21B 47/0005; G01N 2291/02863; G01N 29/11
(Continued)

(56) References Cited

U.S. PATENT DOCUMENTS 3,343,627 A    9/1967    Schroeder
3,883,841 A    5/1975    Norel et al.
(Continued)

FOREIGN PATENT DOCUMENTS

AU    2006276218 B2    1/2012
WO    WO-2007/015796 A2    2/2007

OTHER PUBLICATIONS

"U.S. Appl. No. 11/457,731, Non-Final Office Action mailed Dec. 29, 2008", 7 pgs.
(Continued)

*Primary Examiner* — Ian J Lobo

(57) ABSTRACT

An ultrasonic imaging method is provided. A wideband acoustic pulse is fired at a wall. A wideband response signal is received. The wideband response signal is processed to select an impedance measurement frequency. A wavelet having a characteristic frequency approximately equal to the impedance measurement frequency is fired. A wavelet response signal is received. A reflection coefficient is determined from the wavelet response signal. An impedance measurement is calculated from the reflection coefficient. Related tools and systems are also disclosed.

12 Claims, 6 Drawing Sheets

Related U.S. Application Data division of application No. 11/457,731, filed on Jul. 14, 2006, now Pat. No. 7,656,747.

(60) Provisional application No. 60/701,717, filed on Jul. 22, 2005.

(51) Int. Cl.
  *G01N 29/11* (2006.01)
  *G01N 29/34* (2006.01)
  *G01N 29/44* (2006.01)
  *G01N 29/46* (2006.01)
  *G01V 1/00* (2006.01)

(52) U.S. Cl.
  CPC ......... *G01N 29/4427* (2013.01); *G01N 29/46* (2013.01); *G01V 1/00* (2013.01); *G01N 2291/02863* (2013.01); *G01N 2291/044* (2013.01); *G01V 1/40* (2013.01); *G01V 2210/542* (2013.01)

(58) Field of Classification Search
  USPC .............................................. 367/35; 181/105
  See application file for complete search history.

(56) References Cited

U.S. PATENT DOCUMENTS

| | | | |
|---|---|---|---|
| 4,255,798 A * | 3/1981 | Havira | E21B 47/0005 181/105 |
| 4,709,357 A * | 11/1987 | Maki, Jr. | G01V 1/48 181/105 |
| 4,912,683 A * | 3/1990 | Katahara | E21B 47/082 181/105 |
| 5,144,589 A | 9/1992 | Hardage | |
| 5,146,432 A | 9/1992 | Kimball et al. | |
| 5,216,638 A | 6/1993 | Wright | |
| 5,357,482 A * | 10/1994 | O'Sullivan | G01V 1/50 181/105 |
| 5,644,550 A * | 7/1997 | Priest | G01V 1/50 181/105 |
| 5,675,554 A | 10/1997 | Cole et al. | |
| 5,798,982 A | 8/1998 | He et al. | |
| 5,874,676 A | 2/1999 | Maki, Jr. | |
| 6,041,861 A | 3/2000 | Mandal et al. | |
| 6,125,079 A | 9/2000 | Birchak et al. | |
| 6,131,659 A | 10/2000 | Johnson | |
| 6,188,643 B1 | 2/2001 | Liang et al. | |
| 6,661,737 B2 | 12/2003 | Wisniewski et al. | |
| 6,876,928 B2 | 4/2005 | Van Riel et al. | |
| 7,656,747 B2 | 2/2010 | Mandal et al. | |
| 8,576,660 B2 * | 11/2013 | Mandal | G01N 29/11 367/29 |
| 2003/0147480 A1 | 8/2003 | Richards et al. | |
| 2004/0174770 A1 | 9/2004 | Rees | |
| 2007/0019506 A1 | 1/2007 | Mandal et al. | |
| 2010/0061183 A1 | 3/2010 | Mandal et al. | |

OTHER PUBLICATIONS

"U.S. Appl. No. 11/457,731, Notice of Allowance mailed Jul. 21, 2009", 4 pgs.
"U.S. Appl. No. 11/457,731, Response filed Mar. 27, 2009 to Non-Final Office Action mailed Dec. 29, 2008", 6 pgs.
"U.S. Appl. No. 11/457,731, Response filed Sep. 19, 2008 to Restriction Requirement mailed Sep. 11, 2008", 6 pgs.
"U.S. Appl. No. 11/457,731, Restriction Requirement mailed Sep. 11, 2008", 9 pgs.
"U.S. Appl. No. 12/621,746, Advisory Action mailed Jan. 14, 2013", 2 pgs.
"U.S. Appl. No. 12/621,746, Advisory Action mailed Apr. 29, 2011", 4 pgs.
"U.S. Appl. No. 12/621,746, Amendment Under 37 C.F.R. Sec. 1.312 filed Sep. 25, 2013", 3 pgs.
"U.S. Appl. No. 12/621,746, Final Office Action mailed Mar. 3, 2011", 11 pgs.
"U.S. Appl. No. 12/621,746, Final Office Action mailed Oct. 25, 2012", 11 pgs.
"U.S. Appl. No. 12/621,746, Non Final Office Action mailed Apr. 20, 2012", 9 pgs.
"U.S. Appl. No. 12/621,746, Non Final Office Action mailed Aug. 11, 2011", 10 pgs.
"U.S. Appl. No. 12/621,746, Non-Final Office Action mailed Jul. 8, 2010", 9 pgs.
"U.S. Appl. No. 12/621,746, Notice of Allowance mailed Jun. 25, 2013", 9 pgs.
"U.S. Appl. No. 12/621,746, Pre-Appeal Brief Request for Review filed Jun. 3, 2011", 5 pgs.
"U.S. Appl. No. 12/621,746, Response filed Jan. 3, 2011 to Non Final Office Action mailed Jul. 8, 2010", 7 pgs.
"U.S. Appl. No. 12/621,746, Response filed Apr. 18, 2011 to Final Office Action mailed Mar. 3, 2011", 7 pgs.
"U.S. Appl. No. 12/621,746, Response filed Aug. 13, 2012 to Non Final Office Action mailed Apr. 20, 2012", 7 pgs.
"U.S. Appl. No. 12/621,746, Response filed Oct. 13, 2011 to Non-Final Office Action mailed Aug. 11, 2011", 10 pgs.
"U.S. Appl. No. 12/621,746, Response filed Dec. 19, 2012 to Final Office Action mailed Oct. 25, 2012", 5 pgs.
"Australian Application Serial No. 2006276218, First Examiner Report mailed Sep. 14, 2010", 2 pgs.
"Australian Application Serial No. 2006276218, Response filed Jul. 27, 2011 to Examination Report mailed Sep. 14, 2010", 10 pgs.
"International Application Serial No. PCT/US2006/027629, International Preliminary Report on Patentability dated Jan. 22, 2008", 5 pgs.
"International Application Serial No. PCT/US2006/027629, International Search Report mailed Mar. 6, 2007", 1 pg.
"International Application Serial No. PCT/US2006/027629, Written Opinion mailed Mar. 6, 2007", 4 pgs.

\* cited by examiner

ULTRASONIC IMAGING IN WELLS OR TUBULARS

CROSS-REFERENCE TO RELATED APPLICATIONS

This application includes subject matter related to the following applications, which are hereby incorporated by reference: U.S. Provisional Patent Application No. 60/707,717, dated Jul. 22, 2005, entitled "Ultrasonic Imaging in Wells or Tubulars," by Mandai et al.; U.S. Pat. No. 6,041,861, dated Mar. 28, 2000, entitled "Method to determine self-calibrated circumferential cased bond impedance," by Mandai et al.; U.S. Pat. No. 6,661,737, dated Dec. 9, 2003, entitled "Acoustic Logging Tool Having Programmable Source Waveforms," by Wisniewski, et al. Moreover this application is a continuation application of U.S. patent application Ser. No. 12/621,746, filed Nov. 19, 2009, which application is a divisional application of U.S. patent application Ser. No. 11/457,731, filed Jul. 14, 2006, now issued as U.S. Pat. No. 7,656,747, which application claims the benefit of priority under 35 U.S.C. 119(e) to U.S. Provisional Application No. 60/701,717, filed Jul. 22, 2005 all of which applications are incorporated herein by reference in their entirety.

BACKGROUND

It is often desirable to determine the thickness of a pipe in a well and the properties of materials that surround the pipe, or the well. For example, it may be desirable to determine whether the exterior of a pipe is in contact with fluids or solids, and if so, what type of fluids or solids. Thinning of a pipe due to corrosion may indicate a potential collapse of the pipe. In a downhole context, it may be desirable to determine whether the pipe is tightly bonded to surrounding cement. These are just some examples of when it may be desirable to measure (or even image) through a pipe, or solid tubing wall.

One method for performing such measurements employs an acoustic transducer. Unfortunately, existing technology is limited to pipes having walls less than 0.9 inches thick.

BRIEF DESCRIPTION OF THE DRAWINGS

For a more complete understanding of the present disclosure and the advantages thereof, reference is now made to the following brief description, taken in connection with the accompanying drawings and detailed description, wherein like reference numerals represent like parts.

FIG. 1A shows an acoustic scanning tool embodiment.

DETAILED DESCRIPTION

It should be understood at the outset that although implementations of various embodiments of the present disclosure is described below, the present system may be implemented using any number of techniques, whether currently known or in existence. The present disclosure should in no way be limited to the implementations, drawings, and techniques described below, but may be modified within the scope of the appended claims along with their full scope of equivalents.

The present disclosure provides an ultrasonic imaging method that may be used for pipes having walls greater than 0.9 inches thick. In some embodiments, an acoustic transducer generates a wideband acoustic pulse to determine an impedance measurement frequency for a pipe wall, and then generates a wavelet having a characteristic frequency approximately equal to the impedance measurement frequency for the pipe wall. A processor determines a casing thickness from the inter-peak time in the wavelet response signal. The processor also determines a reflection coefficient from the wavelet response signal. Then the processor calculates an impedance measurement from the reflection coefficient, where the impedance measurement indicates whether the exterior of the pipe is in contact with fluids or solids, and if so, what type of fluids or solids, even if the pipe has walls greater than 0.9 inches thick. The processor may further associate position and orientation information with the impedance measurements to generate an image.

Figure 1:
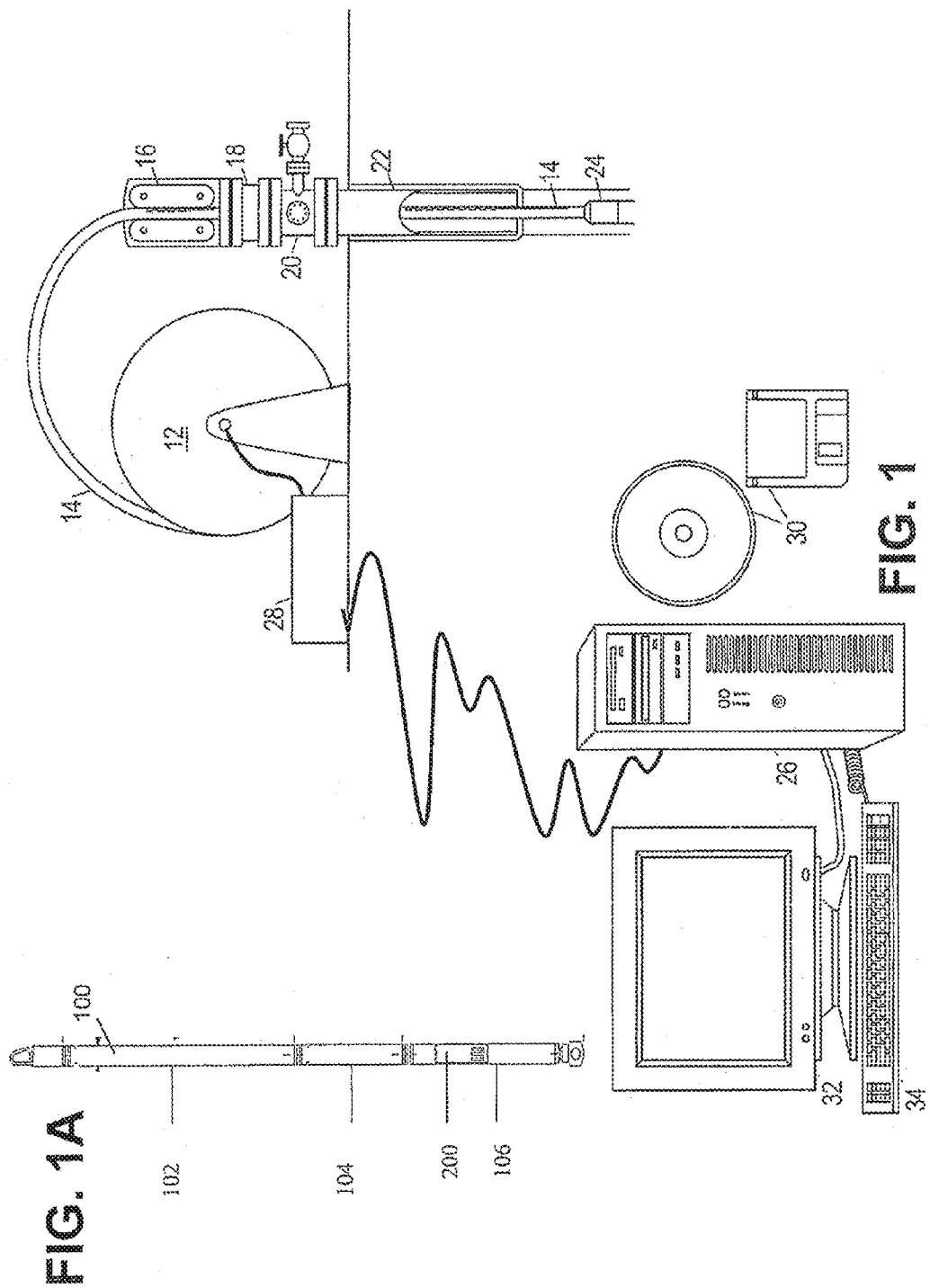
FIG. 1 shows a pipe-conveyed logging environment.

Turning now to the figures, FIG. 1 illustrates a typical pipe-conveyed logging environment. Continuous tubing 14 is pulled from a spool 12 and injected into a wellbore by an injector 16. The tubing 14 is injected through a packer 18 and a blowout preventer 20, and passes through a casing 22 into the wellbore. In the well, a downhole instrument 24 is coupled to tubing 14. The downhole instrument 24 may be configured to communicate to a surface computer system 26 via information conduits contained in the tubing 14. A power supply 28 may be provided to supply power to the downhole instrument 24 via power conduits in the tubing 14. Alternatively, the power and telemetry may be conveyed by a wireline attached to the surface of the tubing 14.

The surface computer system 26 may be configured to communicate with the downhole instrument 24. The downhole instrument 24 may include several downhole sensors and control devices. The surface computer system 26 may be configured by system control software 30 to monitor and control instruments in the downhole instrument 24. The system 26 may include a user-output device 32 and a user-input device 34 to allow a human operator to interact with the software 30. The surface computer system 26 may provide programmable acquisition parameters, including programmable record time for receive signals, programmable sampling intervals, and programmable spatial coverage (resolution).

FIG. 1A shows one embodiment of an acoustic scanning tool 100. The acoustic scanning tool 100 may be one of the downhole sensors included in the downhole instrument 24. The acoustic scanning tool 100 may be divided into sections, including: a main electronics section 102, a directional sub section 104, an acoustic transducer 200, and a second acoustic transducer 106. The acoustic scanning tool 100 has an interchangeable head that may rotate a full 360 degrees and contains the acoustic transducer 200 to provide a full 360 degree profile of the casing 22 or the borehole surrounding the casing 22. A turning motor may rotate the acoustic scanning tool 100.

The main electronics section 102 controls the acquisition of the waveform data by the acoustic transducer 200 and communication with the surface computer system 26. The signals from the acoustic transducer 200 may be digitized using high resolution (e.g., 16 bit) analog-to-digital converters (ADC) and transmitted to the surface computer system 26. The directional sub section 104 provides orientation measurements that enable the surface computer system 26 to generate images from measurements by the acoustic transducer 200. In some logging conditions, the images produced may consist of 200 points horizontally by 40 samples per foot vertically. The second acoustic transducer 106 may be mounted in the acoustic scanning tool 100 to measure characteristics of any borehole fluid to produce real-time fluid travel time (FTT) measurements, as an alternative to using FTT estimates supplied by the surface computer system 26. The second acoustic transducer 106 may also measure borehole fluid impendence to correct measured data.

The data acquisition speed for the surface computer system 26 may be limited by the net telemetry rate, the desired depth sampling rate, the rate for rotating the acoustic transducer 200, the rate for pulling the acoustic transducer through the well, and/or the processing power of the surface computer system 26. In one embodiment, the acoustic transducer 200 may employ piezoelectric elements designed to operate in downhole conditions. However, other transducers that are suitable for downhole operation may be used. The acoustic transducer 200 may be configured to switch back and forth between transmit and receive modes.

The main electronics section 102 fires the acoustic transducer 200 periodically, thereby producing acoustic pressure waves that propagate through the borehole fluid and into the casing 22 and the surrounding formation. At the inner casing wall, some of the acoustic energy is converted into waves that travel through the formation, and some of the acoustic energy is converted into reverberations that propagate back to the acoustic scanning tool 100. As these reflections propagate back to the acoustic scanning tool 100, they cause pressure variations that may be detected by the acoustic transducer 200. The signals received by the acoustic transducer 200 may be processed by the surface computer system 26 to determine the characteristics of the casing 22 and the formation surrounding the casing 22.

Figure 2:
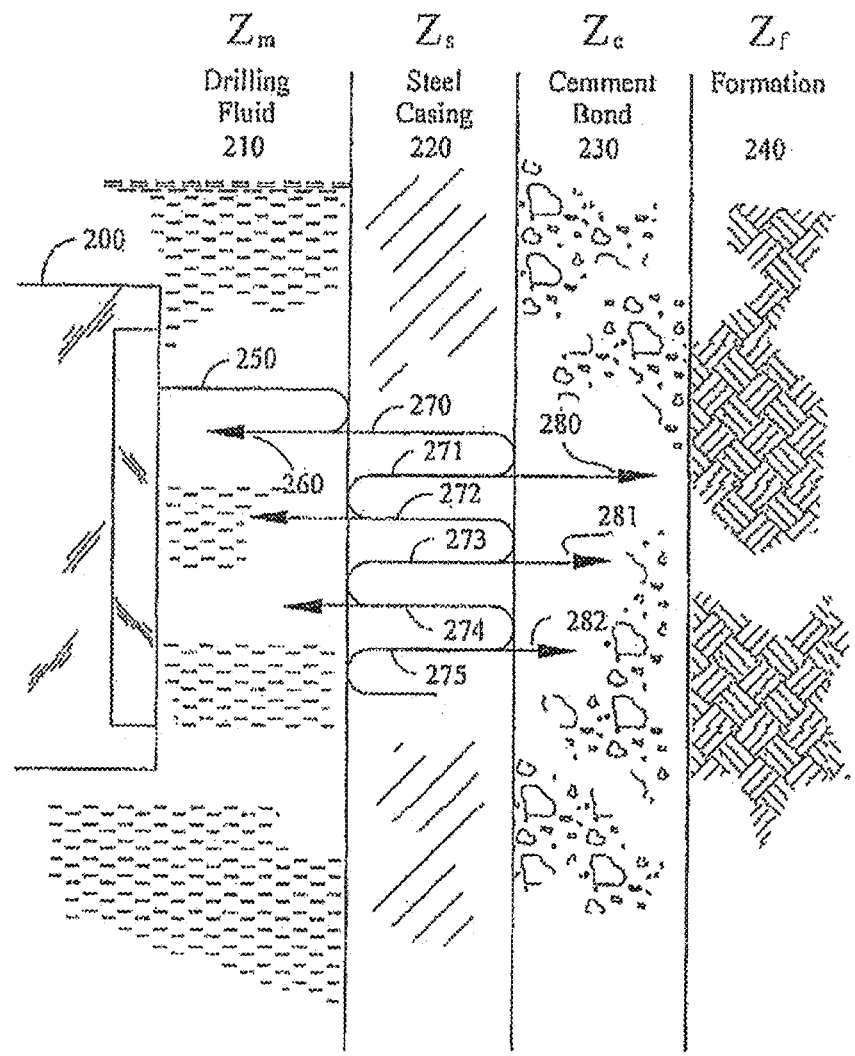
FIG. 2 shows an acoustic transducer transmitting an acoustic pulse through a fluid-casing-cement configuration.

FIG. 2 illustrates an acoustic wave path with casing reflections for a downhole acoustic wave. Shown are the acoustic transducer 200, a drilling fluid 210, a steel casing 220, a cement bond 230, and a portion of a surrounding formation 240. Although depicted as steel casing 220, the casing 22 may be composed of materials other than steel, may be in the form of a pipe, or tubular, and may be referred to as a wall or a casing wall. The drilling fluid 210 (which could alternatively be production fluid) acts as a transmission medium while occupying the area between the acoustic transducer 200 and the steel casing 220, an area referred to as the annulus. The drilling fluid 210, the steel casing 220, the cement bond 230, and the surrounding formation 240 each have a corresponding impedance, labeled $Z_m$, $Z_s$, $Z_c$, and $Z_f$, respectively. Also shown is an acoustic pulse 250, including a first reflected portion 260, casing wave portions 270, 271, 272, 273, 274, 275 and cement wave portions 280, 281, 282. Reflections of cement wave portions 280-282 also propagate through the cement, although this is not explicitly shown.

To measure the impedance of cement or other material outside of the steel casing 220, the acoustic transducer 200 acts as a transmitter to send out the acoustic pulse 250, with a characteristic frequency in the range between 195 to 650 kHz, (or in some implementations, 100 kHz to 750 kHz) then switches to the receive mode. The acoustic pulse 250 frequency is focused on an expected resonance frequency of the steel casing 220. The acoustic pulse 250 travels through the drilling fluid 210 and strikes the steel casing 220. The largest portion of the energy of the acoustic pulse 250 is reflected back to the acoustic transducer 200 as the reflected portion 260 while a small amount of signal enters the steel casing 220 as the casing wave portion 270. When the drilling fluid 210 is water, the reflected portion 260 has an expected amplitude of about 93% of the acoustic pulse 250.

The portion of the acoustic pulse 250 that enters the steel casing 220 is reflected back and forth between the steel casing 220/drilling fluid 210 interface and the steel casing 220/cement bond 230 interface, as illustrated by the casing wave portions 271-275. At each reflection some energy is transmitted through the interface, dependent on the acoustic impedance contrast, and is either directed back toward the acoustic transducer 200 or out to the cement bond 230. The casing wave portions 271-275 inside the steel casing 220 are quickly dissipated in this manner at a rate directly dependent on the acoustic impedance of the material outside the steel casing 220 according to the equation:

$$R_1 = (Z_1 - Z_2)/(Z_1 + Z_2) \quad (1)$$

where $R_1$=the reflective coefficient, and $Z_1$ and $Z_2$ are the impedances of the materials at the interface in question.

The acoustic transducer 200, now acting as a receiver, detects an acoustic response, a waveform consisting of a sequence of exponentially decaying peaks, beginning with the loud initial reflection. The peak to peak times equal twice the travel time through the steel casing 220.

Figure 3:
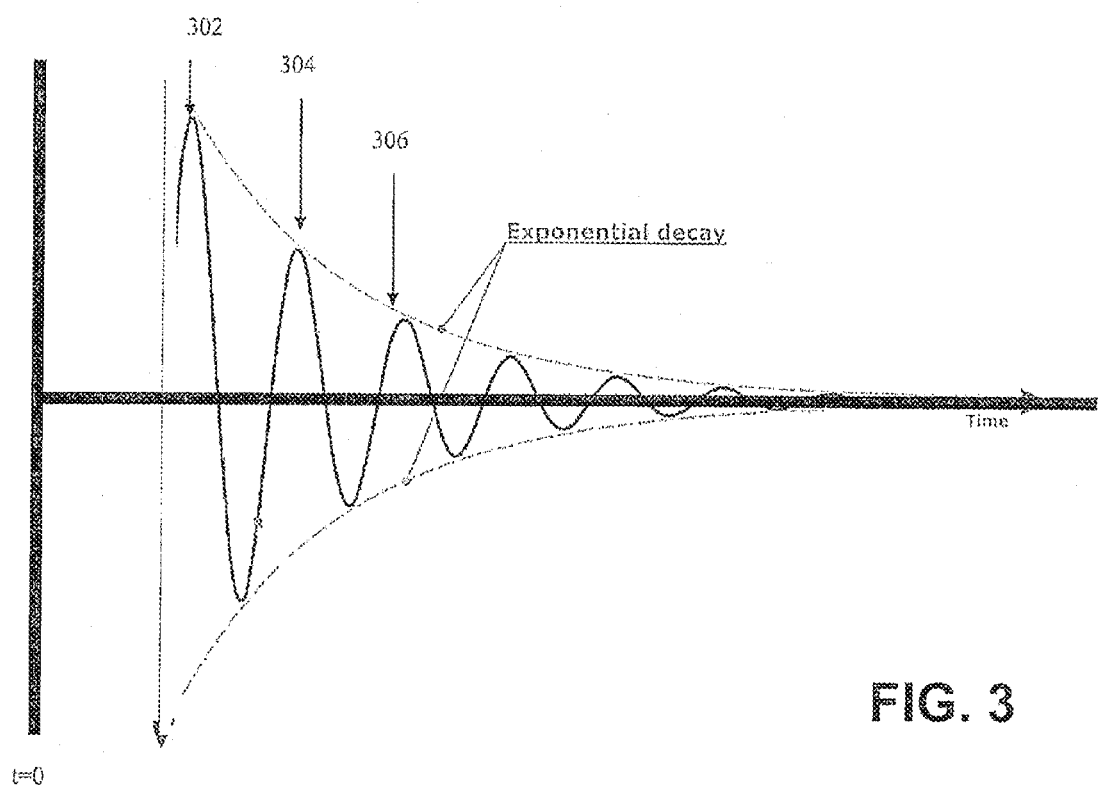
FIG. 3 shows illustrative acoustic response component waves received by an acoustic transceiver.

A distinguishing feature between the illustrative acoustic response waveforms shown in FIG. 3 is the casing thickness relative to the characteristic wavelength of the acoustic pulse 250 from the acoustic transceiver 200. For a casing thickness that is on the order of a ½ wavelength of the acoustic transceiver 200 frequency, the acoustic response waveform may be expected to be an exponentially-decaying oscillatory signal. For a casing thickness that is much higher than the ½ wavelength (also assuming the acoustic transducer 200 ring-down time is less than the two-way travel time of the casing wave), the waveform may be expected to be a pulse train with exponentially-decaying amplitudes. The decay rate of such a pulse train may be relatively straightforward to measure, as it is calculable as the amplitude ratio between neighboring pulses (not including a first pulse amplitude 302), such as the ratio between a second pulse amplitude 304 and a third pulse amplitude 306. This decay rate is directly proportional to the reflectivity coefficient given in equation (1), so with a known acoustic impedance for the steel casing 220, the impedance is readily determined for the cement bond 230. If the impedance determined for a portion of the cement bond 230 is lower then the determined impedances for the surrounding portions of the cement bond 230, the lower impedance may indicate that the cement bond 230 has corroded at the portion with the lower impedance.

The acoustic transducer 200 may be fired repeatedly as the acoustic transducer 200 rotates and moves along the steel casing 220, enabling measurements to be taken over many points on the steel casing 220. Such measurements may be used to create a log and/or image of the steel casing 220 and the material on the outside of the steel casing 220

The surface computer system 26 uses the relationship between the wavelength and the frequency of a wave when selecting the frequency of the wave generated or transmitted. The wavelength of a wave is the distance between repeating units of a wave. Because the frequency of a wave is the number of peaks of a wave to pass a point in a given time, the wavelength of a wave has an inverse relationship to the frequency of a wave. Therefore, when the surface computer system 26 doubles the frequency for a wave, the wavelength of the wave is divided in half.

It has been discovered that fundamental reverberation mode measurements of thick-walled casings would require high power, low frequency transducers with a long listening time Many transducers do not function as accurately at low frequencies, and long listening times produce more signal noise. Ultrasonic measuring systems that operate at the fundamental reverberation mode (i.e. the frequency at which the wavelength is twice the casing thickness) are feasible only for casings having thicknesses below about 0.8 inches. For example, a frequency of 236 kHz may produce the fundamental reverberation mode for a casing, that is 0.474 inches thick, but a casing that is 0.948 inches thick may require a frequency of 118 kHz, which is a frequency that is so low that the signal strength for the reverberation portion of the wave becomes a problem. Additionally, the requirement for a long listening time results in slower data acquisition speed and more noise.

Instead of decreasing the frequency of a wave to operate at the fundamental reverberation mode for a thick casing, embodiments of the present disclosure increase the frequency of a wave to operate at a high order reverberation mode, which is an non-unitary integer multiple of the fundamental reverberation mode. For example, rather than operating at the fundamental reverberation mode by selecting a wavelength of 1.896 inches for a casing that is 0.948 inches thick, an embodiment of the present disclosure may select a wavelength of 0.948 inches, one half of the wavelength of 1.896 inches required for the fundamental reverberation mode. Because the wavelength is reduced through division by two, the frequency is increased though multiplication by two. Multiplying the low frequency of 118 kHz required for the fundamental reverberation mode by two results in a frequency of 236 kHz, a mid-range frequency that does not share the signal strength problems associated with the low frequencies around 118 kHz. Because the wavelength of the wave equals the thickness of the casing, when the reflected portion of the wave travels twice the distance of the thickness of the casing, the reflected portion of the wave completes two full periods of the wavelength. Completing two full periods creates constructive interference, which produces a stronger receive signal at the acoustic scanning tool 100. If the frequency required for the fundamental reverberation mode is multiplied by three, the reflected portion of the wave completes three full periods in each round trip through the casing.

Noise in the signal for a pulse train with exponentially-decaying amplitudes may be filtered out by using a theoretical response for the pulse train. The theoretical prediction of the reflection waves is obtained by multiplying the frequency domain source signal, $S(\omega)$, with the frequency domain theoretical response, $R(\omega)$. This is equivalent to a convolution in the time domain of the acoustic transducer 200 wavelet with the impulse response of the impedance profile shown in FIG. 2. Assuming a flat casing, the theoretical frequency domain response of normal incidence wave may be modeled by the following expression:

$$R(\omega) = \frac{Z_m - Z_s}{Z_m + Z_s} + \frac{\frac{4Z_m Z_s}{(Z_m + Z_s)^2} \cdot \frac{Z_s - Z_c}{Z_s + Z_c}}{\left(1 - \frac{Z_s - Z_m}{Z_m + Z_s} \cdot \frac{Z_s - Z_c}{Z_s + Z_c} \cdot e^{-i2\omega \frac{C_t}{V_s}}\right)} \cdot e^{-i2\omega \frac{C_t}{V_s}} \quad (2)$$

where
$R(\omega)$=the reflection coefficient for any angular frequency w, $Z_m$, $Z_s$, $Z_c$=impedances for the drilling fluid 210, the steel casing 220, and the material on the outside of the steel casing 220, respectively, and $V_s$=the speed of sound in the steel casing 220.

In this expression, $V_s$ is the velocity of sound wave in the steel casing 220 and $C_t$ is the steel casing 220 thickness. In equation (2), $e^{-i2\omega C/V}$ represents the phase delay of two way travel time inside the steel casing 220, and the algebraic expressions of Z's are the reflection coefficients along the boundary. For large casing thickness (longer delay) and a high frequency acoustic transducer (smaller width wavelets, producing waveforms like first response wavelet 402 and second response wavelet 404), the expression (2) may be simplified to represent just the first two pulses in the pulse train:

$$R(\omega) = \frac{Z_m - Z_s}{Z_m + Z_s} + \frac{4Z_m Z_s}{(Z_m + Z_s)^2} \cdot \frac{Z_s - Z_c}{Z_s + Z_c} \cdot e^{-i2\omega \frac{C_t}{V_s}} \quad (3)$$

The $2^{nd}$ term in equation (3) is proportional to the reflection coefficient between the steel casing 220 and the material outside of the steel casing 220. Thus, the second pulse may be measured as a robust indicator of the reflection coefficient, which in turn enables a determination of the impedance for the material on the outside of the steel casing 220 when the steel casing 220 impedance is known or assumed.

In some embodiments, then, the ultrasonic logging tool is provided with a high frequency acoustic transducer having a narrow bandwidth. The period of the source wavelet produced from this high frequency acoustic transducer is less than an expected two-way travel time of sound in the casing, causing the acoustic response waveform to take the form of a pulse train. The casing thickness may be calculated from the time difference between two pulses in the pulse train, where the first pulse represents a reflection from the steel casing 220/drilling fluid 210 interface and the second pulse represents the reflection from the steel casing 220/cement bond 230 interface. A reflection coefficient and/or impedance for the material outside the steel casing 220 is calculated from the amplitude of the second pulse in the receive waveform in comparison to the amplitude of the first pulse.

Figure 4:
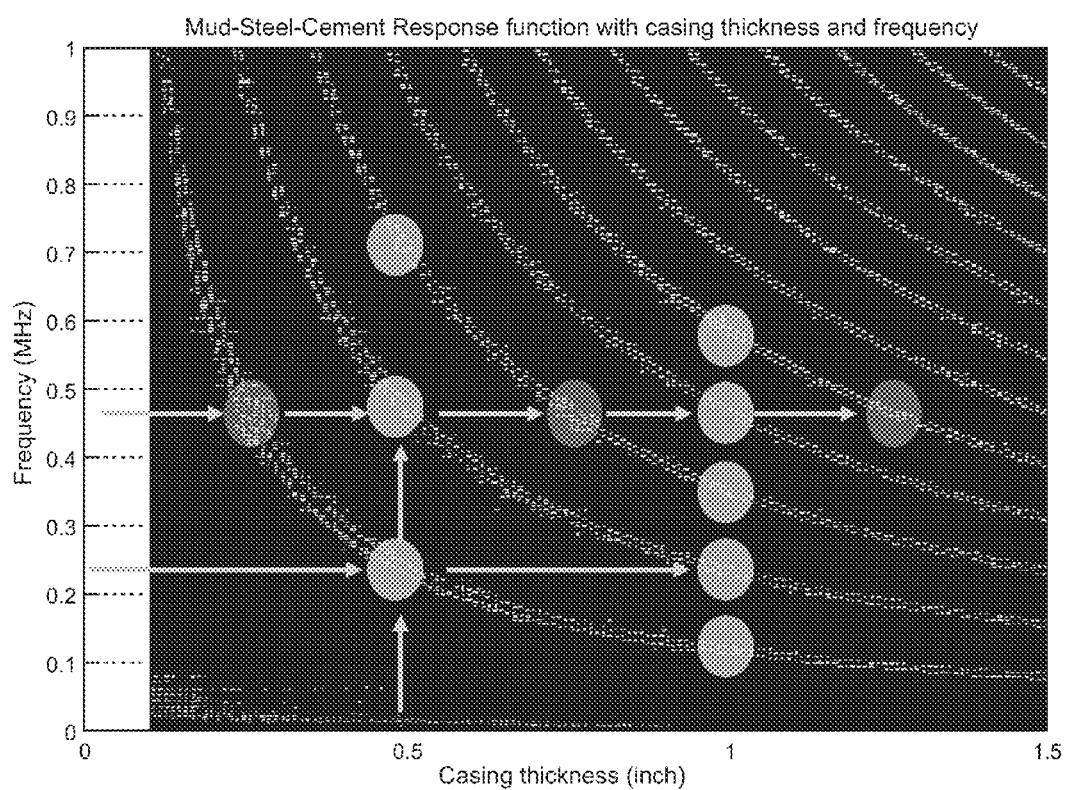
FIG. 4 shows an illustrative frequency response of the fluid-steel-cement configuration for different frequencies and thicknesses.

In some embodiments of the present disclosure, ultrasonic measuring systems use higher order reverberation modes. Expression (2) reveals higher-order reverberation modes that propagate in the steel casing 220. These reverberation modes exist independently of the signal pulse width, and do not necessarily require pulse separation in the acoustic response signal. FIG. 4 is an illustrative color plot of equation (2) as a function of casing thickness and acoustic wavelet frequency. Lighter colors indicate higher amplitudes of $R(\omega)$, and thereby identify a fundamental reverberation mode and various high-order reverberation modes. For example, a 0.5 inch casing may have dominant signals near 240 kHz, or 0.240 MHz, (the fundamental mode) and near other higher order modes (480 kHz, 720 kHz) as illustrated in FIG. 4. Similarly, a 240 kHz transducer may excite 0.5 and 1 inch casing. Note that a 480 kHz (~0.5 MHz) acoustic transceiver may obtain measurable responses from 0.25, 0.5, 0.75, 1.0, and 1.25 inch casing. That is, a carefully chosen acoustic transducer frequency enables a given logging tool to perform ultrasonic imaging for casings of many different standard thicknesses.

Some embodiments of the present disclosure provide for excitation of higher-order reverberation modes, thereby enabling impedance measurements through thick casings without requiring a high-power, low-frequency acoustic transducer. Such embodiments may advantageously enable one acoustic transducer frequency used for measurements with multiple casing wall thicknesses. In some embodiments of the present disclosure, the logging tool may employ a programmable waveform source such as that described in U.S. Pat. No. 6,661,737, to generate wideband signals, e.g., chirp signals, bandpass white-noise pulses, or "impulse" signals. These wideband signals may be used to identify the casing reverberation modes, which may then be used to select a narrowband pulse frequency for impedance measurements. The selected frequency may correspond to an identified reverberation mode or some non-unitary integer multiple thereof.

Figure 5:
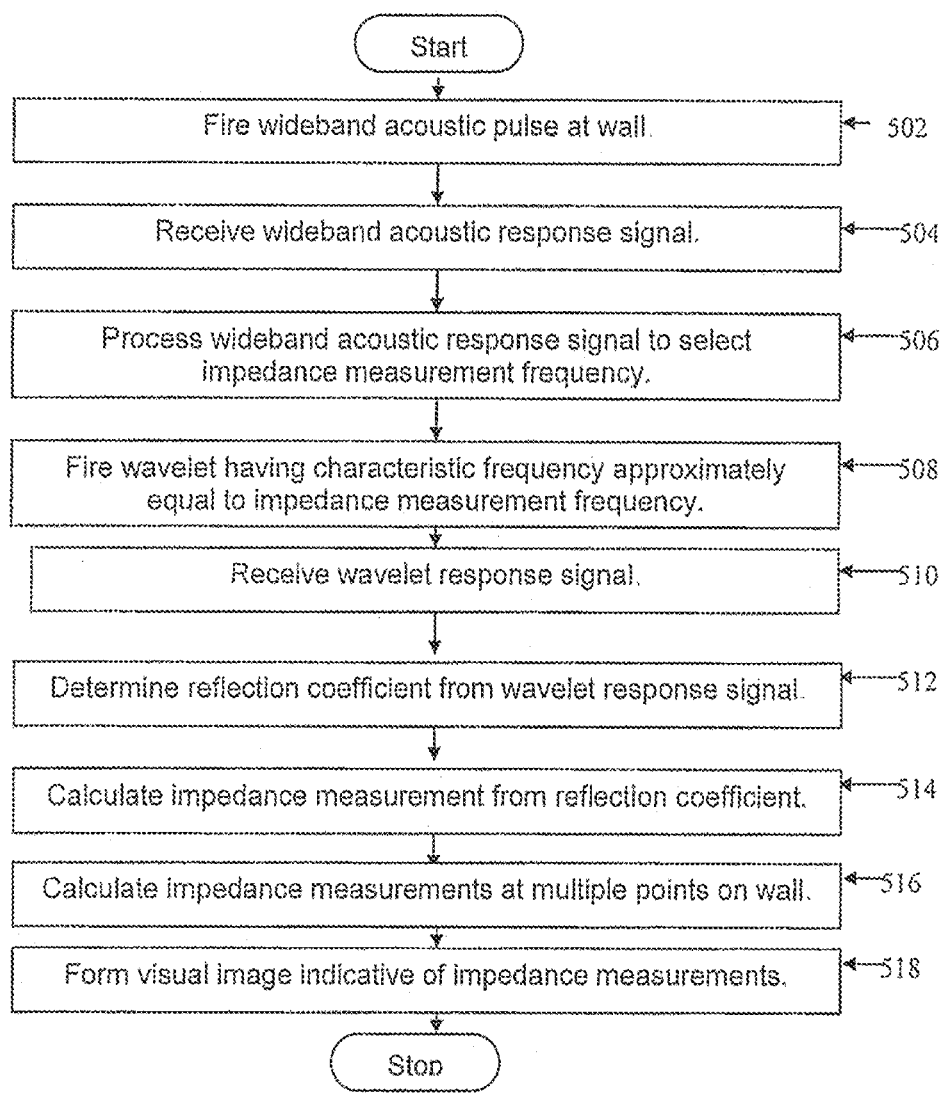
FIG. 5 shows an ultrasonic imaging method for wells or tubulars according to an embodiment of the present disclosure.

FIG. 5 shows an ultrasonic imaging method for wells or tubulars according to an embodiment of the present disclosure. In box 502, the acoustic transducer 200 fires a wideband acoustic pulse at a wall. The wideband acoustic pulse may be a chirp signal. The wall may be thicker than 0.9 inches when using embodiments of the present disclosure.

In box 504, the acoustic transducer 200 receives a wideband acoustic response signal. The acoustic transducer 200 may digitize the wideband acoustic response signal to send a representation of the wideband acoustic response signal to a processor.

In box 506, the processor processes the wideband acoustic response signal to select an impedance measurement frequency. The processor may use a Fourier transform of the wideband response signal to identify peaks in the frequency domain. The peaks may represent high-order reverberation modes. A wavelet is a representation of a signal that is scaled and translated to match the input signal for a decaying oscillating waveform. Based on an identified peak in the frequency domain, the processor selects an impedance measurement frequency for a wavelet.

In box 508, the acoustic transducer 200 fires a wavelet having a characteristic frequency approximately equal to the impedance measurement frequency. The wavelet may have an effective time width less than a two-way travel time of sound in the wall.

In box 510, the acoustic transducer 200 receives a wavelet response signal. The wavelet response signal may be a pulse train. The inter-pulse spacing may be indicative of the wall thickness. The acoustic transducer 200 may digitize the wavelet response signal to send a representation of the wavelet response signal to the processor. Additionally, the acoustic transducer 200 determines the transit time, the time for the travel of the wavelet to the steel casing 220 wall and its time to return back to the acoustic transducer 200.

As such, the transit time provides an indication of the downhole distance between the acoustic transducer 200 and the steel casing 200 wall. Multiple measurements of the transit time enable the processor to determine borehole geometry (ovality), eccentricity and borehole deviation. The processor may combine multiple measurements of the inter-pulse spacing, indicative of the wall thickness, with the transit time, indicative of the downhole distance between the acoustic transducer 200 and the steel casing 220 wall to produce cross-sectionals of the pipe shape and the pipe wall. The processor may also use these combined multiple measurements to determine the average, maximum, and minimum values of the pipe radius and thickness.

In box 512, the processor determines a reflection coefficient from the wavelet response signal. The processor may determine a peak amplitude ratio and a decay rate from the wavelet response signal to determine the reflection coefficient. The processor may convolve a model wavelet with a model response to obtain a model receive signal, compare the model receive signal to the received wavelet response signal, and adjust at least one parameter of the model response to reduce a difference between the model receive signal and the wavelet response signal. The parameters may include a parameter for thickness and a parameter for impedance. The processor may perform impedance inversion by adjusting parameters of a model until a model response matches the acoustic responses. The second pulse in the wavelet response pulse train may have an amplitude indicative of a cement impedance. Because the $2^{nd}$ term in equation (3) is proportional to the reflection coefficient between the steel casing 220 and the material outside of the steel casing 220, the second pulse may be measured as a robust indicator of the reflection coefficient.

In box 514, the processor calculates the impedance measurement from the reflection coefficient. The reflection coefficient enables a determination of the impedance for the material on the outside of the steel casing 220, such as cement, when the steel casing 220 impedance is known or assumed by using equation (1).

In box 516, the processor calculates impedance measurements at multiple points on the wall. The processor may calculate impedance measurements at multiple points on the wall by repeating the method from box 502 to box 514 for each point on the wall.

In box 518, the processor forms a visual image indicative of the impedance measurements. The processor may form a visual image indicative of the impedance measurements by accumulating the calculated impedance measurements and wall thicknesses at multiple points on the wall.

Figure 6:
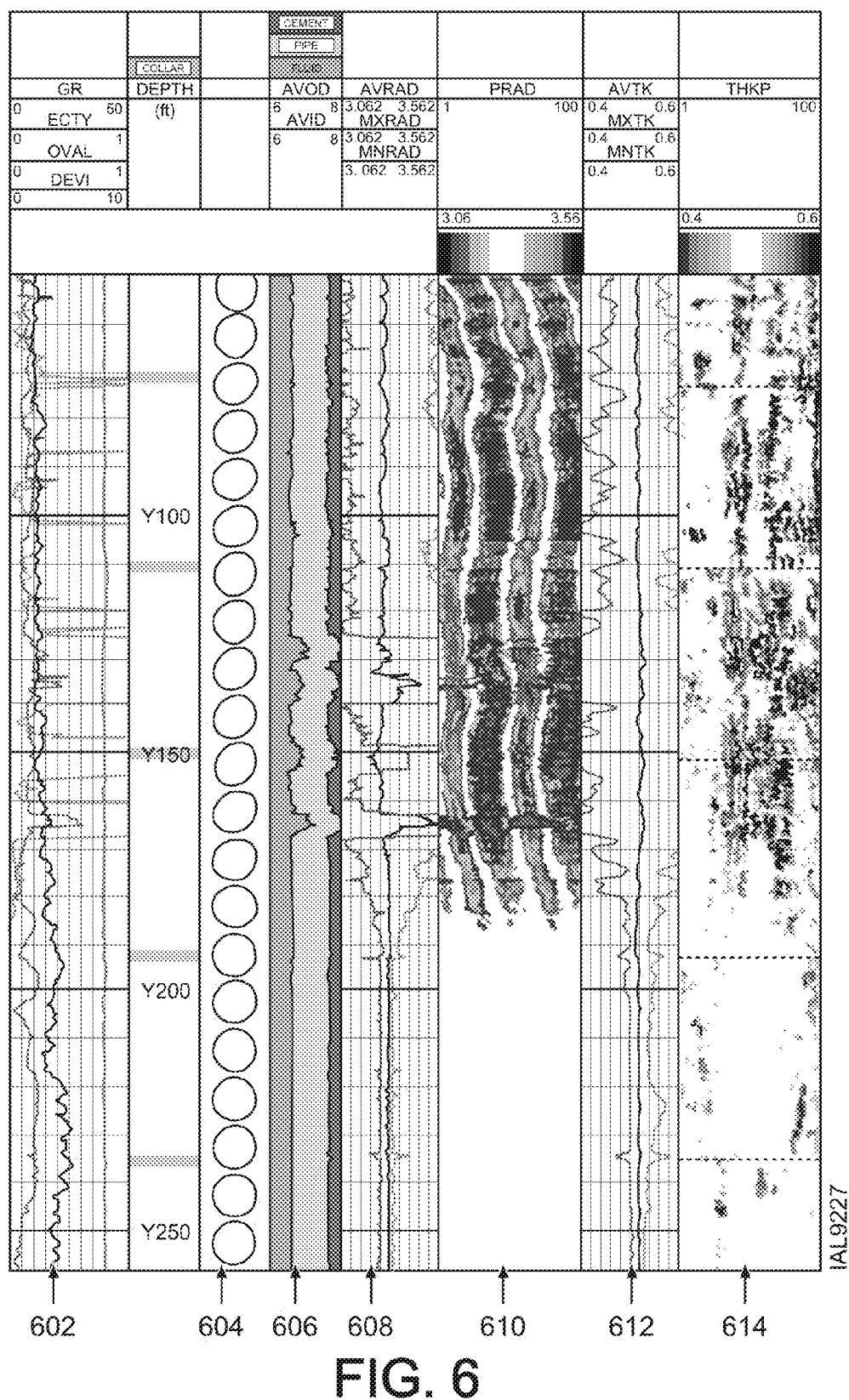
FIG. 6 shows an illustrative casing-evaluation presentation.

FIG. 6 shows an illustrative casing-evaluation presentation. FIG. 6 includes visual images that may be formed by executing the method in FIG. 6, specifically box 518. The data in FIG. 6 may be depicted for casing walls more than 0.9 inches thick by using an embodiment of the present disclosure. Track 602 depicts casing ovality, eccentricity, and hole deviation. In this example, the eccentricity is composed of both tool and casing eccentricity due to formation movement. Track 604 depicts a cross-sectional presentation of the pipe shape. Track 606 depicts a cross-sectional of the pipe wall. Track 608 provides the average, minimum, and maximum value of the pipe radius that is shown in track 610. Track 612 provides the average, minimum and maximum value of the pipe thickness that is the image plotted in track 614. On the image logs, red may show pipe thinning while blue may show pipe thickening.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein, but may be modified within the scope of the appended claims along with their full scope of equivalents. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as directly coupled or communicating with each other may be coupled through some interface or device, such that the items may no longer be considered directly coupled to each other but may still be indirectly coupled and in communication, whether electrically, mechanically, or otherwise with one another. Other examples of changes, substitutions, and alterations are ascertainable by one skilled in the art and could be made without departing from the spirit and scope disclosed herein.

What is claimed is:

1. A method comprising:
    transmitting a waveform pulse from an acoustic transducer, the waveform pulse comprising a wavelet having a characteristic frequency that is a non-unitary integer multiple of a fundamental reverberation frequency of a casing having a thickness;
    receiving an acoustic response, having a second peak following a first peak, in response to transmitting the waveform pulse;
    determining, using a processor, an inter-peak time and an amplitude of the second peak in the acoustic response; and
    determining, using the processor, an impedance value from the amplitude, with the impedance value being at least one of an impedance value of the casing and an impedance value of material surrounding the casing.

2. The method of claim 1, wherein the method includes determining the thickness of the casing from the inter-peak time.

3. The method of claim 1, wherein the method includes determining, using the processor, the characteristic frequency.

4. The method of claim 1, wherein the method includes using a second acoustic transducer to measure characteristics of borehole fluid to produce real-time fluid travel time measurements.

5. The method of claim 1, wherein transmitting a waveform pulse from an acoustic transducer includes a waveform provided as a programmable waveform.

6. A method comprising:
    transmitting acoustic pulses from an acoustic transducer of an acoustic logging tool, the acoustic pulses comprising wavelets having a characteristic frequency that is a non-unitary integer multiple of a fundamental reverberation frequency of a casing wall of a casing;
    digitizing, using the acoustic transducer, acoustic responses received in response to transmitting the acoustic pulses;
    receiving representations of the acoustic responses at a surface facility; and
    determining, using the surface facility, acoustic impedance measurements of material around the casing.

7. The method of claim 6, wherein the method includes determining the characteristic frequency from a thickness of the casing wall, and determining the thickness from an inter-peak time of the acoustic responses.

8. The method of claim 6, wherein the method includes performing impedance inversion, using the surface facility, by adjusting parameters of a model until a model response matches the acoustic responses.

9. The method of claim 6, wherein the characteristic frequency is designed to excite different reverberation modes in different standard casing wall thicknesses.

10. The method of claim 6, wherein the method includes determining, using the surface facility, the impedance measurements through a casing wall thicker than 0.9 inches.

11. The method of claim 6, wherein transmitting acoustic pulses from an acoustic transducer of an acoustic logging tool includes using an logging tool having programmable acquisition parameters including programmable record time for receive signals, programmable sampling interval, and programmable spatial coverage (resolution).

12. The method of claim 6, wherein the method includes using a second acoustic transducer to measure characteristics of borehole fluid to produce real-time fluid travel time measurements.

* * * * *